United States Patent
Ha et al.

(10) Patent No.: US 10,793,537 B1
(45) Date of Patent: Oct. 6, 2020

(54) METHOD OF ACID SACCHARIFICATION OF BIOMASS

(71) Applicant: KOREA INSTITUTE OF SCIENCE AND TECHNOLOGY, Seoul (KR)

(72) Inventors: Jeong-Myeong Ha, Seoul (KR); Hyemin Yang, Seoul (KR); Ye Seul Jeong, Seoul (KR); Jae Wook Choi, Seoul (KR); Dong Jin Suh, Seoul (KR); Young Hyun Yoon, Seoul (KR); Gi Seok Yang, Seoul (KR); Ung Lee, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 0 days.

(21) Appl. No.: 16/683,260

(22) Filed: Nov. 14, 2019

(30) Foreign Application Priority Data

Oct. 1, 2019 (KR) .................. 10-2019-0121602

(51) Int. Cl.
  *C07D 307/50* (2006.01)
  *C07H 3/02* (2006.01)
(52) U.S. Cl.
  CPC ............ *C07D 307/50* (2013.01); *C07H 3/02* (2013.01)
(58) Field of Classification Search
  CPC ................ C07D 307/50; C07H 3/02
  USPC ........................................................ 549/506
  See application file for complete search history.

(56) References Cited

U.S. PATENT DOCUMENTS

| 2012/0316372 A1 | 12/2012 | Corma Canos et al. |
| 2013/0252302 A1* | 9/2013 | Pan .................. C12P 7/10 435/165 |

FOREIGN PATENT DOCUMENTS

| KR | 1020090039470 A | 4/2009 |
| KR | 101734908 B1 | 5/2017 |
| KR | 102006860 B1 | 8/2019 |

OTHER PUBLICATIONS

Avelino Corma et al., "High-Quality Diesel from Hexose- and Pentose-Derived Biomass Platform Molecules," ChemSusChem, 2011, pp. 1574-1577, vol. 4.

(Continued)

*Primary Examiner* — Taylor V Oh
(74) *Attorney, Agent, or Firm* — Cantor Colburn LLP

(57) ABSTRACT

Disclosed herein are a method of acid saccharification of biomass and a method of polymerization of furan compounds. The method of acid saccharification of biomass comprises recovering pentose-derived furan compounds produced during the acid saccharification process of biomass. The method of acid saccharification of biomass comprises introducing furan compounds into the acid saccharification process of biomass, to produce and recover furan polymers.

13 Claims, 2 Drawing Sheets xylose → furfural   2-methylfuran
(dehydration, hydrogenation)

Trimer 1

Trimer 2

(56) References Cited

OTHER PUBLICATIONS

Avelino Corma et al., "Production of High-Quality Diesel from Biomass Waste Products," Angew. Chem. Int. Ed., 2011, pp. 2375-2378, vol. 50.

Guangyi Li et al., "Synthesis of High-Quality Diesel with Furfural and 2-Methylfuran from Hemicellulose," ChemSusChem, 2012, pp. 1958-1966, vol. 5.

Guangyi Li et al., "Synthesis of renewable diesel with the 2-methylfuran, butanal and acetone derived from lignocellulose," Bioresource Technology, 2013, pp. 66-72, vol. 134.

Inaki Gandarias et al., "Production of 2-methylfuran from biomass through an integrated biorefinery approach," Fuel Processing Technology, 2018, 8 pages, Elsevier B.V.

M. J. Campos Molina et al., "Cyclopentyl methyl ether: A green co-solvent for the selective dehydration of lignocellulosic pentoses to furfural," Bioresource Technology, 2012, pp. 321-327, vol. 126, Elsevier Ltd.

\* cited by examiner

Trimer 1

Trimer 2

METHOD OF ACID SACCHARIFICATION OF BIOMASS

CROSS-REFERENCE TO RELATED APPLICATION

This application claims the priority to Korean Patent Application No. 10-2019-0121602, filed on Oct. 1, 2019, and all the benefits accruing therefrom under 35 U.S.C. § 119, the contents of which in its entirety are herein incorporated by reference.

BACKGROUND

Field

Disclosed herein are a method of acid saccharification of biomass and a method of polymerization of furan compounds.

DESCRIPTION OF GOVERNMENT-SUPPORTED RESEARCH AND DEVELOPMENT

This study was conducted by the support of the Ministry of Trade, Industry and Energy (Specialized Institution for Management of Research: Korea Energy Technology Evaluation and Planning, Title of Study: Development of Technology for Catalytic Chemical Reaction for Making High-Carbon Transportation Fuel from Furan Compounds Derived from Unfermented Sugars, Project Number: 20163010092210) under the supervision of the Korea Institute of Science and Technology.

DESCRIPTION OF THE RELATED ART

Woody biomass, which is nonedible biomass, allows to produce sugars from carbohydrates which take up about 70% thereof. In addition, the resultant sugars can be used as a raw material of bioalcohols, biochemical products, etc. The acid saccharification process, which is a chemical saccharification method, has been widely studied as one of the methods for producing carbohydrates and sugars from woody biomass. The acid saccharification process has the advantage of allowing to quickly obtain a saccharified solution by means of a chemical process, but involves problems such as the production of furan by-products during the saccharification process and necessity for separation of the acid used as a catalyst.

Meanwhile, although the glucose obtained from woody biomass can be used as a raw material of bioalcohols, it is difficult to convert the pentose obtained therefrom, such as xylose, through a biological process. Accordingly, technologies for utilizing furan compounds, such as furfural, that can be obtained from pentose by dehydration have been developed. For example, technologies for production of furan polymers and production of fuels and chemicals therefrom have been studied. Conventional technologies for polymerization of furan were realized through various catalysts and reaction technologies, but the reaction process thereof involves many steps and purification of the reactant furan. Thus, there is a need for development of an economical and efficient process.

SUMMARY

In one aspect, an object of the present disclosure is to provide a method of acid saccharification of biomass, comprising recovering pentose-derived furan compounds produced during the acid saccharification of biomass.

In another aspect, an object of the present disclosure is to provide a method of acid saccharification of biomass, comprising introducing furan compounds into the acid saccharification process of biomass to produce furan polymers.

In one aspect, the technology disclosed herein comprises a method of acid saccharification of biomass, comprising a step of carrying out acid saccharification of biomass in a mixture of two immiscible phases, wherein the mixture of two phases is an acidic aqueous solution that saccharifies biomass with acid and an extraction solution of furan compounds.

In one exemplary embodiment, the extraction solution of furan compounds may comprise one or more selected from the group consisting of hydrophobic ether compounds, alcohol compounds and ketone compounds.

In one exemplary embodiment, the extraction solution of furan compounds may comprise cyclopentylmethylether.

In one exemplary embodiment, the furan compounds may comprise furfural.

In one exemplary embodiment, the method may comprise a step of adding an extraction solution of furan compounds to an acidic aqueous solution containing biomass to carry out acid saccharification of biomass.

In one exemplary embodiment, the acidic aqueous solution containing biomass may be a suspension obtained by mixing biomass and an acidic aqueous solution and then stirring the resultant at 30 to 150° C.

In one exemplary embodiment, the method may comprise a step of recovering furan compounds from the extraction solution.

In one exemplary embodiment, the method may comprise a step of further adding furan compounds to the acidic aqueous solution containing biomass.

In one exemplary embodiment, the furan compounds may be one or more of furan, 2-methylfuran, and gamma-valerolactone.

In one exemplary embodiment, in the method, the acid saccharification of biomass and the polymerization of furan compounds may be carried out as a one-pot reaction.

In one exemplary embodiment, in the method, one or more of 5,5'-(furan-2-ylmethylene)bis(2-methylfuran) and 5,5-bis(5-methylfuran-2-yl)pentan-2-one may be produced through polymerization.

In one exemplary embodiment, the extraction solution may be added in a volume ratio of 0.5 or more relative to the acidic aqueous solution.

In one exemplary embodiment, the acid saccharification may be carried out at 80 to 150° C. The technology disclosed herein provides a method in which the process conditions are set so that dehydration of pentose simultaneously occurs during the acid saccharification process of woody biomass, and in which the polymerization of the furan compounds produced during the saccharification process is carried out in a one-pot reaction manner. Thus, the technology disclosed herein has the effect of increasing the utilization of the furan compounds produced in the acid saccharification process and securing the economic feasibility of the overall process of utilizing biomass.

In one aspect, the technology disclosed herein has the effect of providing a method of acid saccharification of biomass, comprising separating and purifying the pentose-derived furan compounds produced during the acid saccharification process of biomass.

In another aspect, the technology disclosed herein has the effect of providing a method of acid saccharification of biomass, comprising introducing furan compounds into the acid saccharification process of biomass, to produce furan polymers.

BRIEF DESCRIPTION OF THE DRAWINGS

In FIG. 1, Trimer 1 denotes $C_{15}H_{14}O_3$ (5,5'-(furan-2-ylmethylene)bis(2-methylfuran)), which may be produced by polymerization of two 2-methylfurans and one furfural.

In FIG. 1, Trimer 2 denotes $C_{15}H_{18}O_3$ (5,5-bis(5-methylfuran-2-yl)pentan-2-one), which may be produced by polymerization of three 2-methylfurans

DETAILED DESCRIPTION

Figure 1:
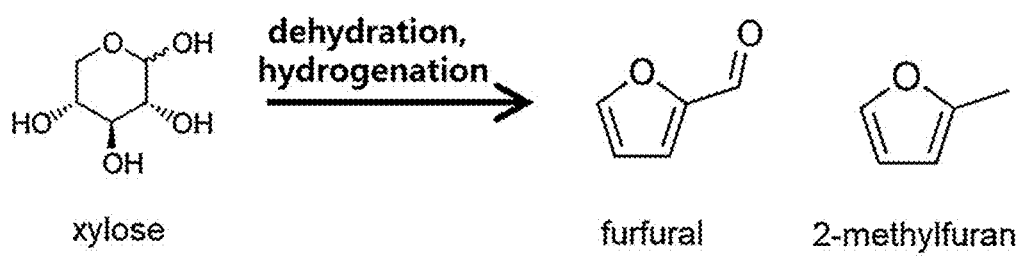
FIG. 1 illustrates a production process of furan compounds according to one example of the present disclosure and products thereof. In one exemplary embodiment, furfural may be produced by dehydration of xylose. In another exemplary embodiment, 2-methylfuran may be produced by selective hydrogenation of furfural.
Figure 1:
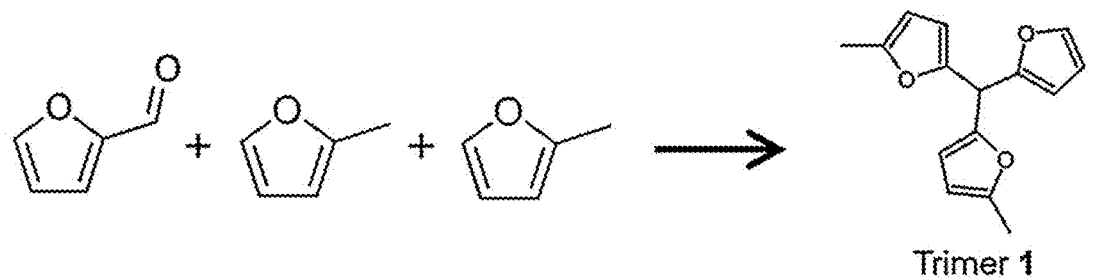
Figure 1:
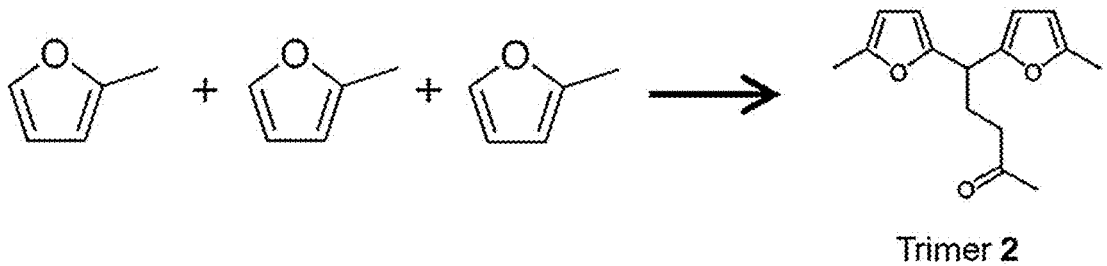
Figure 2:
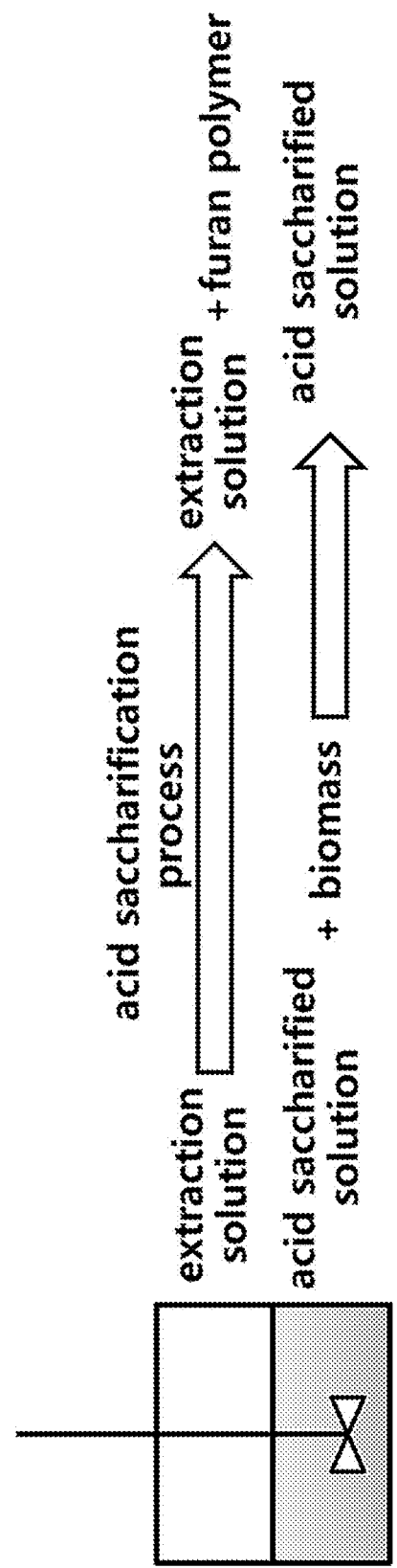
FIG. 2 illustrates a method of acid saccharification according to one example of the present disclosure.

Hereinafter, the present invention will be described in detail.

In one aspect, the technology disclosed herein provides a method of acid saccharification of biomass, comprising a step of carrying out acid saccharification of biomass in a mixture of two immiscible phases, wherein the mixture of two phases is an acidic aqueous solution that saccharifies biomass with acid and an extraction solution of furan compounds.

Conventional acid saccharification processes of biomass are intended for the production of sugars. In the processes, the furan compounds obtained from pentose and hexose are regarded as impurities to be removed from the saccharified solution. Thus, conventional acid saccharification processes of biomass aim at carrying out the reaction under the conditions where furan compounds are produced as little as possible.

In contrast, the acid saccharification process of biomass according to the present disclosure is a method allowing to utilize the furan compounds produced by the dehydration of pentose. It further induces the production of furan compounds from pentose by carrying out acid saccharification at a higher temperature. Also, it allows to directly polymerize the resultant furan compounds, for example, furfural, and remove them from the saccharified solution. Thus, acid saccharification, dehydration, and polymerization are sequentially carried out in the same reactor in a one-pot sequential reaction manner, allowing to produce furan polymers in the acid saccharification process of biomass.

As used herein, "two phases" refers to a state in which the two layers of an acidic aqueous solution and an extraction solution immiscible with the acidic aqueous solution exist together without being mixed with each other.

In one exemplary embodiment, the biomass may be woody biomass and comprise wood, herbs, etc.

In one exemplary embodiment, the biomass may comprise *Miscanthus giganteus*.

In one exemplary embodiment, the acidic aqueous solution may comprise an acid catalyst.

In one exemplary embodiment, the acid catalyst may be a homogeneous catalyst that is completely dissolved in water or a heterogeneous catalyst that is not dissolved in water.

In one exemplary embodiment, the acid catalyst may be a homogeneous catalyst comprising one or more selected from the group consisting of sulfuric acid, hydrochloric acid, nitric acid, phosphoric acid, lactic acid, acetic acid, citric acid, formic acid, and oxalic acid.

In one exemplary embodiment, the acid catalyst may be a heterogeneous catalyst comprising a solid acid.

In one exemplary embodiment, the solid acid may be one or more selected from the group consisting of silica, alumina, silica-alumina, zirconia, titania, zeolite, and magnesium oxide.

As used herein, the "extraction solution of furan compounds" refers to a solution capable of extracting the furan compounds contained in an acidic aqueous solution, and which is not mixed with an acidic aqueous solution to forms two phases.

In one exemplary embodiment, the extraction solution of furan compounds may comprise one or more selected from the group consisting of hydrophobic ether compounds, alcohol compounds and ketone compounds.

In one exemplary embodiment, the extraction solution of furan compounds may comprise cyclopentylmethylether.

In one exemplary embodiment, the furan compounds may comprise furfural.

In one exemplary embodiment, the method may comprise a step of adding an extraction solution of furan compounds to the acidic aqueous solution containing biomass to carry out acid saccharification of biomass. The "acidic aqueous solution containing biomass" may refer to a suspension or acid saccharified solution in which biomass and an acidic aqueous solution are well mixed.

In one exemplary embodiment, the acidic aqueous solution containing biomass may be a suspension obtained by mixing biomass with an acidic aqueous solution and then stirring the resultant at 30 to 150° C., or 50 to 150° C., or 30 to 120° C., or 50 to 120° C.

In one exemplary embodiment, the acidic aqueous solution containing biomass may be a suspension obtained by mixing biomass with an acidic aqueous solution and then stirring the resultant at 50 to 1,000 rpm.

In one exemplary embodiment, the method may comprise a step of recovering furan compounds from the extraction solution. The method of acid saccharification of biomass according to the present disclosure has the effect of increasing the yield of furan compounds and allowing to easily recover furan compounds.

In one exemplary embodiment, the method may comprise a step of further adding furan compounds as polymerization raw materials to the acidic aqueous solution containing biomass. In the method, an extraction solution of furan compounds and furan compounds may be added to the acidic aqueous solution containing biomass, to carry out acid saccharification of biomass.

In one exemplary embodiment, the furan compounds may be one or more of furan, 2-methylfuran, and gamma-valerolactone.

In one exemplary embodiment, in the method, it may be preferable to add 2-methylfuran to the acidic aqueous solution containing biomass. Polymerization of the furfural produced by the addition of 2-methylfuran can prevent a reaction which forms a resin.

In one exemplary embodiment, in the method, the acid saccharification of biomass and the polymerization of furan compounds may be carried out as a one-pot reaction.

In one exemplary embodiment, the method may be a method of polymerization of furan compounds.

In the method of acid saccharification of biomass according to the present disclosure, the furan by-products produced during the acid saccharification process of biomass comprising a carbohydrate may be directly polymerized and separated during the saccharification process.

In one exemplary embodiment, in the method, the furfural produced by the dehydration of sugars and the added furan compounds may be polymerized through polymerization, or the added furan compounds may be polymerized, to produce high carbon compounds.

In one exemplary embodiment, in the method, one or more of 5,5'-(furan-2-ylmethylene)bis(2-methylfuran) and 5,5-bis(5-methylfuran-2-yl)pentan-2-one may be produced through polymerization.

In one exemplary embodiment, the method may comprise a step of recovering one or more of furfural, 5,5'-(furan-2-ylmethylene)bis(2-methylfuran) and 5,5-bis(5-methylfuran-2-yl)pentan-2-one from the extraction solution.

In one exemplary embodiment, preferably, the extraction solution may be added in a volume ratio of 0.5 or more, or 0.5 to 10, relative to the acidic aqueous solution. In one exemplary embodiment, the extraction solution may be added in a volume ratio of 0.5 or more, 1 or more, 1.5 or more, or 2 or more and 10 or less, 9 or less, 8 or less, 7 or less, 6 or less, 5 or less, 4 or less, 3 or less, 2 or less, or 1 or less, relative to the acidic aqueous solution. For example, the volume ratio of the extraction solution and the acidic aqueous solution may be 0.5 to 2:1.

In one exemplary embodiment, the acid saccharification may be carried out at 80 to 150° C., or 100 to 150° C. Thus, it is possible to prevent conversion of glucose or further decomposition or carbonization of the furfural produced from pentose, which results from excessively high temperature, and carry out acid saccharification and the polymerization of furan compounds in a one-pot reaction manner.

In one exemplary embodiment, preferably, the acid saccharification may be carried out for 30 minutes or more, or 30 minutes to 24 hours, or 30 minutes to 10 hours, or 60 minutes to 6 hours. In one exemplary embodiment, the acid saccharification may be carried out for a time period of 30 minutes or more, or 60 minutes or more and 24 hours or less, 20 hours or less, 16 hours or less, 12 hours or less, 8 hours or less, 4 hours or less, or 1 hour or less.

In one exemplary embodiment, the acid saccharification may be carried out by stirring at 50 rpm or more, or 50 to 1,000 rpm. In one exemplary embodiment, the acid saccharification may be carried out by stirring at 50 rpm or more, 100 rpm or more, 150 rpm or more, 200 rpm or more, 250 rpm or more, or 300 rpm or more and 1,000 rpm or less, 900 rpm or less, 800 rpm or less, 700 rpm or less, 600 rpm or less, 500 rpm or less, 400 rpm or less, or 300 rpm or less.

In one exemplary embodiment, the sugars may be one or more selected from the group consisting of glucose, galactose, mannose, xylose, arabinose and fructose.

Hereinafter, the present invention will be described in detail by way of examples. It will be apparent to those skilled in the art that these examples are for illustrative purposes only, and the scope of the present invention is not construed as being limited by these examples.

Example 1: Acid Saccharification of Biomass

An acid saccharification process of woody biomass was carried out. *Miscanthus giganteus* was used as the biomass raw material. A suspension in which a *Miscanthus giganteus* sample in a solid state and a sulfuric acid solution are well mixed was prepared by mixing 17.3 g of a *Miscanthus giganteus* sample and 20 mL of an 80% by weight sulfuric acid solution and stirring the resultant at 30° C. and 75 rpm for 30 minutes. Then, 55.6 mL of ion-exchanged water was added to dilute the aqueous sulfuric acid solution to a concentration of 30% by weight, and 8.74 to 151.2 mL of cyclopentylmethylether ($C_5H_9OCH_3$, CPME) was added to adjust the volume ratio of CPME and the acidic aqueous solution to 0.2-2. Acid saccharification was carried out by stirring the resultant at 80 to 120° C. and 500 rpm for 30 to 120 minutes. The acid saccharification and the dehydration of sugars were carried out as a one-pot reaction. After the reaction was completed, the resultant was cooled to room temperature, and then the acidic aqueous solution layer and the CPME layer were analyzed by GC and HPLC.

TABLE 1

| No. | Miscanthus giganteus (g) | CPME/ acidic aqueous solution (v/v) | Acidic aqueous solution (mL) | CPME (mL) | Reaction temperature (° C.) | Reaction time (min) | Xylose yield (%)[1] | Glucose yield (%)[2] | Furfural yield (%)[3] |
|---|---|---|---|---|---|---|---|---|---|
| 1 | 17.3 | 2 | 75.6 | 151.2 | 100 | 30 | 34.2 | 61.6 | 9.43 |
| 2 | 17.3 | 0.5 | 75.6 | 37.8 | 120 | 30 | 35.0 | 65.9 | 2.77 |
| 3 | 4.0 | 0.5 | 17.48 | 8.74 | 100 | 30 | 40.3 | 67.9 | 2.66 |
| 4 | 4.0 | 0.5 | 17.48 | 8.74 | 100 | 30 | 38.3 | 49.9 | 3.48 |
| 5 | 4.0 | 0.5 | 17.48 | 8.74 | 100 | 60 | 36.0 | 65.5 | 6.05 |
| 6 | 4.0 | 0.5 | 17.48 | 8.74 | 100 | 120 | 24.1 | 49.6 | 4.64 |

[1]Yield as the percentage of the weight of the produced xylose relative to the weight of the xylose contained in biomass, as measured by the NREL method. Sum of the mass measured from each of the aqueous solution layer and the CPME layer.
[2]Yield as the percentage of the weight of the produced glucose relative to the weight of the glucose contained in biomass, as measured by the NREL method. Sum of the mass measured from each of the aqueous solution layer and the CPME layer.
[3]Yield as the percentage of the weight of the produced furfural relative to the weight of the xylose contained in biomass, as measured by the NREL method. Sum of the mass measured from each of the aqueous solution layer and the CPME layer.

produced xylose relative to the weight of the xylose contained in biomass, as measured by the NREL method. Sum of the mass measured from each of the aqueous solution layer and the CPME layer.

[2]Yield as the percentage of the weight of the produced glucose relative to the weight of the glucose contained in biomass, as measured by the NREL method. Sum of the mass measured from each of the aqueous solution layer and the CPME layer.

[3]Yield as the percentage of the weight of the produced furfural relative to the weight of the xylose contained in biomass, as measured by the NREL method. Sum of the mass measured from each of the aqueous solution layer and the CPME layer.

The results showed that the volume ratio of CPME and the acidic aqueous solution was 0.5 or more. The results also showed that, when acid saccharification was carried out at a temperature of 100 to 120° C., the yield of xylose in the acid saccharification process was 24.1% to 40.3% and the yield of glucose in the process was 49.6% to 67.9%. It was found that xylose was dehydrated at a relatively low temperature of 100 to 240° C. part so that some xylose was converted to furfural, and thus that 2.66% to 9.43% of furfural was produced in the reaction at 100 to 120° C.

Example 2: Method of Acid Saccharification of Biomass in which a Polymerization Process of Furan Compounds is Carried Out Simultaneously The simultaneous polymerization process of furan compounds was carried out as follows during the acid saccharification process of woody biomass. *Miscanthus giganteus* was used as the biomass raw material. A suspension in which a *Miscanthus giganteus* sample in a solid state and a sulfuric acid solution are well mixed was prepared by mixing 4 g of a *Miscanthus giganteus* sample and 4.62 mL of an 80% by weight sulfuric acid solution and stirring the resultant at 30° C. and 75 rpm for 30 minutes. Then, 12.86 mL of ion-exchanged water was added to dilute the aqueous sulfuric acid solution to a concentration of 30% by weight, and 3.5 to 34.96 mL of cyclopentylmethylether ($C_5H_9OCH_3$, CPME) was added to adjust the volume ratio of CPME and the acidic aqueous solution to 0.2-2, followed by addition of 0.1 to 1.0 mL of 2-methylfuran. Acid saccharification was carried out by stirring the resultant at 100° C. and 0 to 1,000 rpm for 30 to 120 minutes. Acid saccharification, dehydration of sugars, and polymerization of furan compounds were carried out as a one-pot reaction. After the reaction was completed, the resultant was cooled to room temperature, and then the acidic aqueous solution layer and the CPME layer were analyzed by GC and HPLC.

TABLE 2

| No. | *Miscanthus giganteus* (g) | CPME/ acidic aqueous solution (v/v) | Acidic aqueous solution (mL) | CPME (mL) | 2-methylfuran (mL) | Reaction temperature (° C.) | Reaction time (min) | Stirring speed (rpm) |
|---|---|---|---|---|---|---|---|---|
| 1 | 4 | 0.5 | 17.48 | 8.74 | 0.38 | 100 | 60 | 300 |
| 2 | 4 | 0.5 | 17.48 | 8.74 | 0.26 | 100 | 60 | 300 |
| 3 | 4 | 2 | 17.48 | 34.96 | 0.26 | 100 | 60 | 300 |
| 4 | 4 | 0.5 | 17.48 | 8.74 | 0.3 | 100 | 60 | 0 |
| 5 | 4 | 0.5 | 17.48 | 8.74 | 0.3 | 100 | 60 | 600 |
| 6 | 4 | 0.5 | 17.48 | 8.74 | 0.3 | 100 | 30 | 300 |
| 7 | 4 | 0.5 | 17.48 | 8.74 | 0.3 | 100 | 120 | 300 |
| 8 | 4 | 0.5 | 17.48 | 8.74 | 0.1 | 100 | 60 | 300 |
| 9 | 4 | 0.5 | 17.48 | 8.74 | 1.0 | 100 | 60 | 300 |
| 10 | 4 | 0.5 | 17.48 | 8.74 | 0.3 | 100 | 60 | 300 |
| 11 | 4 | 0.5 | 17.48 | 8.74 | 0.3 | 100 | 60 | 300 |
| 12 | 4 | 0.5 | 17.48 | 8.74 | 0.3 | 100 | 60 | 300 |
| 13 | 4 | 0.5 | 17.48 | 8.74 | 0.3 | 100 | 60 | 1000 |

TABLE 3

| No. | Xylose yield (%)[1] | Glucose yield (%)[2] | Furfural yield (%)[3] | Trimer 1 yield (%)[4] | Trimer 2 yield (%)[5] | (Furfural yield) + (Trimer 1 yield)/3 (%)[6] |
|---|---|---|---|---|---|---|
| 1 | 24.4 | 51.6 | 5.4 | 2.3 | 3.5 | 6.2 |
| 2 | 26.3 | 59.3 | 5.5 | 2.1 | 4.0 | 6.2 |
| 3 | 26.2 | 59.8 | 12.4 | 4.9 | n.d. | 14.0 |
| 4 | 34.0 | 62.0 | 3.9 | 1.5 | 1.6 | 4.4 |
| 5 | 33.2 | 68.9 | 6.5 | 2.0 | 5.7 | 7.2 |
| 6 | 33.1 | 63.0 | 4.7 | 3.7 | 4.1 | 5.9 |
| 7 | 26.2 | 57.5 | 4.3 | 2.7 | 3.4 | 5.2 |
| 8 | 38.7 | 71.7 | 5.8 | 1.7 | 1.6 | 6.4 |
| 9 | 33.2 | 68.9 | 3.5 | 4.3 | 20.9 | 4.9 |
| 10 | 18.0 | 52.6 | 11.6 | 4.2 | 7.4 | 13.0 |
| 11 | 6.1 | 34.8 | 13.2 | 5.9 | 2.7 | 15.2 |
| 12 | 7.8 | 38.0 | 14.2 | 4.9 | 5.1 | 15.8 |
| 13 | 25.3 | 56.5 | 6.1 | 2.0 | 3.9 | 6.8 |

[1] Yield as the percentage of the weight of the produced xylose relative to the weight of the xylose contained in biomass, as measured by the NREL method. Sum of the mass measured from each of the aqueous solution layer and the CPME layer.
[2] Yield as the percentage of the weight of the produced glucose relative to the weight of the glucose contained in biomass, as measured by the NREL method. Sum of the mass measured from each of the aqueous solution layer and the CPME layer.
[3] Yield as the percentage of the weight of the produced furfural relative to the weight of the xylose contained in biomass, as measured by the NREL method. Sum of the mass measured from each of the aqueous solution layer and the CPME layer.
[4] Yield as the percentage of the weight of the produced Trimer 1 relative to the weight of the xylose contained in biomass, as measured by the NREL method. Mass measured from the CPME layer (Trimer 1 = compound produced by the polymerization of two 2-methylfuran molecules and one furfural molecule).
[5] Yield as the percentage of the weight of the produced Trimer 2 relative to the weight of the xylose contained in biomass, as measured by the NREL method. Mass measured from the CPME layer (Trimer 2 = compound produced by the polymerization of three 2-methylfurans).
[6] Sum of the produced furfural and the furfural consumed to produce the polymer.

produced xylose relative to the weight of the xylose contained in biomass, as measured by the NREL method. Sum of the mass measured from each of the aqueous solution layer and the CPME layer.

[2] Yield as the percentage of the weight of the produced glucose relative to the weight of the glucose contained in biomass, as measured by the NREL method. Sum of the mass measured from each of the aqueous solution layer and the CPME layer.

[3]Yield as the percentage of the weight of the produced furfural relative to the weight of the xylose contained in biomass, as measured by the NREL method. Sum of the mass measured from each of the aqueous solution layer and the CPME layer.

[4]Yield as the percentage of the weight of the produced Trimer 1 relative to the weight of the xylose contained in biomass, as measured by the NREL method. Mass measured from the CPME layer (Trimer 1=compound produced by the polymerization of two 2-methylfuran molecules and one furfural molecule).

[5]Yield as the percentage of the weight of the produced Trimer 2 relative to the weight of the xylose contained in biomass, as measured by the NREL method. Mass measured from the CPME layer (Trimer 2=compound produced by the polymerization of three 2-methylfurans).

[6]Sum of the produced furfural and the furfural consumed to produce the polymer.

The results showed that the yield of Trimer 1, which is a polymer obtained from the xylose-derived furfural produced during the acid saccharification process, was 1.5% to 5.9%. When considering only the part of Trimer 1 derived from furfural, the overall yield of furfural was up to 15.8%, which was improved compared to the yield of the furfural produced in Example 1. Also, it was found that polymerization of furan compounds occurred during the acid saccharification process as some of the furfural produced as a result of the reaction was recovered as polymers.

While the present invention has been described with respect to the specific embodiments, it will be apparent to those skilled in the art that the above descriptions are only preferred embodiments and that the scope of the present invention is not limited thereto. Thus, the scope of the present invention should be defined by the appended claims and equivalents thereof.

What is claimed is:

1. A method of acid saccharification of biomass, comprising:
    preparing a mixture of two immiscible phases; and
    carrying out acid saccharification of the biomass in the mixture of two immiscible phases,
    wherein the first phase is an extraction solution for furan compounds and the second phase is an acidic aqueous solution comprising the biomass, and the first phase is immiscible in the second phase, and
    wherein the extraction solution for furan compounds comprises a hydrophobic ether compound, an alcohol compound, a ketone compound, or a combination thereof.

2. The method of acid saccharification of biomass according to claim 1,
    wherein the extraction solution for furan compounds comprises cyclopentylmethylether.

3. The method of acid saccharification of biomass according to claim 1,
    wherein the furan compounds are furfural.

4. The method of acid saccharification of biomass according to claim 1,
    wherein the preparing comprises adding the extraction solution for furan compounds to the acidic aqueous solution containing biomass.

5. The method of acid saccharification of biomass according to claim 4,
    wherein the acidic aqueous solution containing biomass is a suspension obtained by mixing biomass and an acidic aqueous solution and then stirring the resultant at 30 to 50° C.

6. The method of acid saccharification of biomass according to claim 1,
    wherein the method comprises a step of recovering furan compounds from the extraction solution.

7. The method of acid saccharification of biomass according to claim 4,
    wherein the method comprises a step of further adding a furan compound to the acidic aqueous solution containing biomass.

8. The method of acid saccharification of biomass according to claim 7,
    wherein the furan compound added to the acidic aqueous solution is one or more of furan, 2-methylfuran, and gamma-valerolactone.

9. The method of acid saccharification of biomass according to claim 7,
    wherein, in the method, the acid saccharification of biomass and the polymerization of furan compounds are carried out as a one-pot reaction.

10. The method of acid saccharification of biomass according to claim 9,
    wherein, in the method, one or more of 5,5'-(furan-2-ylmethylene)bis(2-methylfuran) and 5,5-bis(5-methylfuran-2-yl)pentan-2-one are produced through polymerization.

11. The method of acid saccharification of biomass according to claim 4,
    wherein the extraction solution is added in a volume ratio of 0.5 or more relative to the acidic aqueous solution.

12. The method of acid saccharification of biomass according to claim 4,
    wherein the acid saccharification is carried out at 80 to 150° C.

13. The method of acid saccharification of biomass according to claim 1, wherein a volume ratio of the extraction solution to the acidic aqueous solution in the mixture of two immiscible phases is 0.5:1 to 2:1.

* * * * *